US009950074B2

(12) United States Patent
Steinfeld et al.

(10) Patent No.: US 9,950,074 B2
(45) Date of Patent: Apr. 24, 2018

(54) COMPOSITION AND DELIVERY VEHICLE FOR ACTIVE AGENTS AND METHODS THEREFOR

(71) Applicants: Robert Steinfeld, Goettingen (DE); Marcel Grapp, Goettingen (DE)

(72) Inventors: Robert Steinfeld, Goettingen (DE); Marcel Grapp, Goettingen (DE)

(73) Assignees: Georg-August-Universität Göttingen Stiftung Öffenlichen Rechts, Universitätsmedizin, Göttingen (DE); AllOrphan UG, Göttingen (DE)

( * ) Notice: Subject to any disclaimer, the term of this patent is extended or adjusted under 35 U.S.C. 154(b) by 139 days.

(21) Appl. No.: 13/650,193

(22) Filed: Oct. 12, 2012

(65) Prior Publication Data
US 2014/0105817 A1 Apr. 17, 2014

(51) Int. Cl.
| | | |
|---|---|---|
| A61K 51/00 | (2006.01) | |
| A61K 36/14 | (2006.01) | |
| A61K 47/48 | (2006.01) | |
| A61K 47/42 | (2017.01) | |
| G01N 33/68 | (2006.01) | |
| A61K 9/00 | (2006.01) | |
| A61K 47/64 | (2017.01) | |
| A61K 47/69 | (2017.01) | |

(52) U.S. Cl.
CPC ...... *A61K 47/48276* (2013.01); *A61K 9/0085* (2013.01); *A61K 47/42* (2013.01); *A61K 47/6425* (2017.08); *A61K 47/6907* (2017.08); *G01N 33/6893* (2013.01)

(58) Field of Classification Search
CPC ........ A61K 9/00; A61K 9/0085; A61K 47/00; A61K 47/48276; A61K 47/488; A61K 47/42; A61K 47/6425; A61K 47/6907; G01N 33/6893
USPC .... 424/1.11, 1.65, 1.69, 1.73, 9.1, 9.2, 1.21; 514/1, 1.1, 19.2, 19.3, 19.4, 19.5, 19.6
See application file for complete search history.

(56) References Cited

U.S. PATENT DOCUMENTS

| | | | | |
|---|---|---|---|---|
| 2004/0161457 A1* | 8/2004 | Gabizon | .............. | A61K 31/704 424/450 |
| 2006/0062842 A1 | 3/2006 | Gabizon et al. | | |
| 2008/0063868 A1* | 3/2008 | Chung | .................... | B82Y 5/00 428/402 |

FOREIGN PATENT DOCUMENTS

| | | |
|---|---|---|
| EP | 2425817 | 3/2012 |
| WO | 2010/143193 | 12/2010 |
| WO | WO2010/143193 | 12/2010 |
| WO | WO2011/000551 | 1/2011 |
| WO | 2011/097480 | 8/2011 |

OTHER PUBLICATIONS

Steinfield et al (The American Journal of Human Genetics, 2009, vol. 85, pp. 354-363).*
Zhao et al, Expert Opinion on Drug Delivery, 2008, vol. 5, No. 3, pp. 309-319.*
Kelemen, Int. J. Cancer, 2006, vol. 119, pp. 243-250.*
Mueller; "Microvesicles/exosomes as potential novel biomarkers of metabolic diseases"; Diabetes, Metabolic Syndrome and Obesity: Targets and Therapy, Aug. 1, 2012, pp. 247-282.
Steinfeld et al.; "Folate Receptor Alpha Defect Causes Cerebral Folate Transport Deficiency: A Treatable Neurodegenerative Disorder Associated with Disturbed Myelin Metabolism"; The American Journal of Human Genetics, Sep. 1, 2009, vol. 85, No. 3, pp. 354-363.
Patrick et al; "Folate receptors as potential therapeutic targets in choroid plexus tumors of SV40 transgenic mice"; Journal of Neuro-Oncology, pp. 111-123.
Alvarez-Erviti et al.; "Delivery of siRNA to the mouse brain by systemic injection of targeted exosomes"; Nature Biotechnology, Mar. 20, 2011, vol. 29, No. 4, pp. 341-345.

* cited by examiner

*Primary Examiner* — D L Jones
(74) *Attorney, Agent, or Firm* — Whitman, Curtis & Cook, P.C.

(57) ABSTRACT

A vehicle composition in the form of a vesicular composition or a particular composition and, optionally, an active agent associated with the vesicle forming components or particles, and folate receptor alpha is used as a delivery system for the transport of components and/or active agents into the cerebrospinal fluid (CSF) and/or brain and/or central nervous system and/or spinal cord. The composition is used for treating of CSF or brain pertaining diseases, disorders or conditions, such as preventing or treating neurological or neurodegenerative diseases, disorders or conditions.

5 Claims, 4 Drawing Sheets

COMPOSITION AND DELIVERY VEHICLE FOR ACTIVE AGENTS AND METHODS THEREFOR

In a first aspect, the present invention relates to a vehicle composition, in particular, to a vesicular composition or a particular composition comprising either vesicle forming components or particles, optionally, an active agent associated with the vesicle forming components or particles, and folate receptor alpha. In another aspect, the present invention relates to a delivery system for the transport of components and/or active agents into the cerebrospinal fluid (CSF) and/or brain and/or central nervous system and/or spinal cord comprising vesicles or particles and folate receptor alpha, preferably being located on the outer surface of said vesicles or particles. The present invention relates further to a method for the delivery of components and/or active agents, in particular, of active agents into the CSF and/or brain and/or central nervous system and/or spinal cord as well as for treating of CSF and/or brain and/or central nervous system and/or spinal cord pertaining diseases, disorders or conditions. In particular, the present invention relates to a method for preventing or treating neurological or neurodegenerative diseases, disorders or conditions, comprising administering the delivery systems or vehicle composition according to the present invention.

PRIOR ART

Drug delivery systems represent a powerful tool for delivering drugs or other active agents to a desired target. Said delivery systems include vector-based as well as vesicle-based systems. Various kinds of vehicles have been described for targeting the active agents including drugs or prodrugs to the target, e.g. a predetermined cell type or predetermined tissue. For example, incorporation of said active agents by entrapment or encapsulation into suitable means has been used. As suitable means, vesicles, like liposomes, exosomes, etc. have been described for the transport of active agents in biological systems.

Multiple examples are provided in the art describing the usefulness of liposomes or other vesicle-based means for the transport of active agents into the cells. These include also biological gene delivery vehicles. Moreover, said vehicles in form of vesicles, e.g. liposomes, or as particles have been described for targeting diagnostics. Said vehicles including vesicles and particles are common mechanisms to allow transport and predetermined targeting thereof.

For example, exosomes are nano-sized vesicles with typical size of 30-100 nm which can carry other components or active agents, e.g. by incorporation into the lipid membrane, or may contain them in the core thereof. Moreover, various biomedical applications for liposomes have been described wherein said liposomes have other components like receptor ligand molecules at their surface either attached or incorporated in the membrane, respectively.

The active agent may be present in the lipid membrane as well as in the core formed by the lipid membranes. In case of particles, like solids of metals, composites or polymers which may be coated with suitable means, the other components, like receptors or ligands, as well as the active agents may be attached or otherwise associated on the surface thereof.

However, the main obstacle of the vehicles described so far is the targeted delivery. That is, a major hurdle in providing vehicles for target delivery of active components is to avoid any unspecific targeting to cells, tissues or sites. Indeed, one of the most challenging issues in localized drug delivery and specific targeting is achieving delivery of the active agents to the desires place or cells and then, upon delivery, having the particular active agent retaining its activity. That is, without harming other tissues or cells delivering the active components at predetermined sites or cells. This is particularly true in the delivery of agents to the brain because of difficulties in penetrating the blood-brain barrier or blood-CSF barrier. Indeed, the further development of many therapeutic agents has been abandoned because sufficient therapeutic agent levels in the brain could not be achieved via the systemic circulation.

For example, for liposomes or exosomes various approaches have been made, e.g. as described in WO 2011/000551 mentioning an exosome-based treatment of cancer, US 2006/0062842 relating to a method of administering a compound to multidrug resistant cells as well as in WO 2010/143193 relating to targeted liposomes comprising and containing bis-phosphonates and uses thereof.

However, there is still an ongoing need for vehicles allowing drug delivery or delivery of active agents to predetermined targets. This is particularly true for targeting to uncommon places or sides including the cerebrospinal fluid, the spinal cord, central nervous system or brain.

Folates are a group of essential micronutritional compounds that are found in bacteria and plants. Folic acid is a chemically synthesized, oxidized derivative that is converted to 5-methyltetrahydrofolate (5MTHF) by several enzymatic reactions. 5MTHF is the major biological active form that functions as cofactor in many methylation reactions. In particular, nucleotide synthesis and thymidine formation as well as the conversion of homocystein to methionine depend on 5MTHF. The latter reaction is required for the generation of S-adenosylmethionine (SAM) the central methyl-donor in most tissues and subcellular compartments. 5MTHF is distributed by the blood stream to all major organs and transverse membranes by at least three major transport systems. The reduced folate carrier (RFC, SLC19A1) belongs to a group of organic anion transporters (OAT) that exchange 5MTHF with other inorganic or organic anions. The influx Km of the RFC for 5MTHF and other reduced folates is 2-7 µM. Taken the plasma 5MTHF concentration of about 4-20 nM (up to 50 nM during the first year of life) this implies a significant transmembrane anion concentration difference to achieve intracellular uptake of 5MTHF. The uptake of folates into enterocytes in the small intestine is mediated by the proton-coupled folate transporter (PCFT, SLC46A1). This transporter has a pH optimum of 5.5 and functions as proton cotransporter with a Km of about 1 µM. A group of GPI-anchored receptors, folate receptor alpha (FRα), beta (FRβ) and delta (FRδ) induce endocytosis of folates after binding them with high affinity (Kb 1-10 nM) at neutral pH. The function of the secreted folate receptor gamma (FRγ) is currently not understood. In addition, several ABC exporters (MRP1-5 and ABSG2) are capable to transport folates with low affinity.

Recently, cerebral folate transport deficiency, a childhood neurodegenerative disease that is caused by mutations in the FOLR1 gene leading to a functional loss of FRα has been described (Steinfeld et al., 2009). Since the functional loss of FRα is associated with very low 5MTHF concentration in the CSF but normal plasma concentration of 5MTHF and since FRα is most abundantly expressed in the choroid plexus we have hypothesized that FRα is the major route for the blood-CSF transport of 5MTHF. In this study we demonstrate that FRα is essential and sufficient to transport 5MTHF into the CSF and that FRα is additionally required to distribute 5MTHF into the brain parenchyma.

SUMMARY OF THE INVENTION

At present, the disclosure provides, according to a first aspect, a vehicle composition, in particular, vesicular composition or particular composition, comprising vesicle forming components or particles optionally, one or more active agents associated with the vesicle forming components or particles, and folate receptor alpha.

That is, the present inventors recognized that vesicles with folate receptor alpha represent targeted vesicles for specific sites or cells. In particular, it is demonstrated herein that exosomes with folate receptor alpha penetrate into the brain parenchyma and are taken up by astrocytes and neurons. Moreover, it has been demonstrated that exosomes or other types of vehicles including vesicles and particles having folate receptor alpha, preferably, located on the surface of said vehicles, represent a suitable transport medium, in particular, allows exosome targeting of specific cell types.

Surprisingly, the present invention recognized that exosomes secreted from the choroid plexus contain folate receptor alpha. In addition, said folate receptor alpha present on the outer surface of exosomes enables transport of other components or active agents by the cerebrospinal fluid (CSF) to targets in the CSF, brain, central nervous system or spinal cord. That is, vesicles or vesicle composition with folate receptor alpha represents suitable means for transport of other components, in particular, active agents, over the blood-CSF-barrier through the choroid plexus or when injected into the CSF, brain or intrathecally or intracranially or intraventricularly.

Moreover, it has been demonstrated that the targeted liposomes with folate receptor alpha targets specific cell types including astrocytes and neurons. Hence, the present invention provides means and methods for targeting astrocytes, neurons and other brain cells with the vesicle composition or the delivery system as described herein.

As used herein, the term "associated with" describes that the components and/or active agents are either covalently or non-covalently linked with the vehicle or system, or are incorporated, e.g. entrapped or encapsulated, into the vehicles, like being entrapped or encapsulated in the core of vesicles. In case of solid particles, the term "associated with" refers to covalent or non-covalent binding of the components and/or active agents with other moieties of the particles.

As used herein, the term "vehicle" refers to a vehicle composition, in particular, to a vesicular composition or a particular composition comprising either vesicle forming components or particles, optionally, one or more active agents associated with the vesicle forming components or particles, and folate receptor alpha.

With respect to the term "folate receptor alpha" the present invention relates to folate receptor alpha and fragments thereof binding folate. It is preferred that the folate receptor alpha is derived from mammals, in particular, human. Typically, the folate receptor alpha present in the vehicle composition or the drug delivery system according to the present invention or used the methods according to the invention are stemming from the same species than the species to be treated. In particular, the term refers to the human folate receptor alpha of Seq. ID. No. 1, NM_016725.2, e.g. encoded by a sequence of Seq. ID. No. 2.

The term "fragments" refers to polypeptides having a shortened sequence of SEQ ID No. 1 or homologous folate receptor alpha peptides. Said fragments remain their ability to target the vehicle or system to the desired place, e.g. the CSF, brain, CNS or spinal cord.

The term "homologs" refers to folate receptor alpha molecules from other species, e.g. mouse, horse, cow, pig, dogs, cats, etc.

The term "derivatives" refers to peptides containing amino acids exchanges while remaining the folate receptor activity, typically conservative amino acid exchanges as well as to fusion molecules comprising the folate receptor alpha molecules or fragments thereof.

In a preferred embodiment, the present invention provides a vehicle composition, in particular, vesicular composition or particular composition wherein the vesicle forming components are lipids, in particular, vesicles forming membranes. The skilled person is well aware of suitable lipids allowing vesicle formation. For example suitable lipids are described in US 2006/0062842 or WO 2006/143193. Alternatively, the vesicular composition of particular composition according to the present invention relates to vehicle composition wherein the vesicles are exosomes, liposomes, nanostructured vesicles, micelles or erythrocyte ghosts. The particles according to present invention maybe particles selected form organic particles, inorganic particles, colloidal particles, nanoparticles or composite particles.

As used herein, the terms "comprising" or "comprise" or "containing" or "contain" include the embodiment of "consisting" or "consist".

It is preferred, that the vesicles are based on exosomes isolated or obtained from natural sources, produced in cell culture, reconstituted with purified components in vitro or generated with modified liposomes in vitro. The skilled person is well aware of suitable methods for isolation of exosomes and generation of liposomes accordingly. For example WO 2011/097480 describes suitable means and methods therefore. The vehicle composition is characterized in having folate receptor alpha. It is preferred that the folate receptor alpha is located on the outer surface on the vesicle. It has been shown that the presence of folate receptor alpha allows targeting of the vesicles including vesicles or particles into the CSF and the brain as well as into the central nervous system and spinal cord. In particular, it has been recognized that exosomes with folate receptor alpha are transported from the CSF into the brain parenchyma.

The present invention relates in another aspect to a vehicle composition according to the present invention wherein the folate receptor alpha is human folate receptor alpha, in particular, the human folate receptor alpha of SEQ ID No. 1 or fragments thereof. In addition, the folate receptor alpha may be a homolog of said human folate receptor alpha or derivates of the human folate receptor alpha.

The term "active agent" refers on the one hand to pharmaceutically active agents including drugs or prodrugs or magnetic agents or radioactive agents. On the other hand, said active agents include suitable diagnostics. Said suitable diagnostics include marker molecules or optionally being a label, magnetic agents or radioactive agents.

Typically said active agents associated with the vesicle forming components are encapsulated or entrapped in said vesicle forming components formed of lipids. For example, in case of exosomes the active agents are present in the core of the exosomes while the folate receptor alpha being present on the outer surface of said exosomes accordingly.

The vehicles according to the present invention, in particular, the vesicular compositions or particular compositions according to the present invention containing active agents being pharmaceutically active agents including drugs or prodrugs or magnetic agents or radioactive agents are agents for treating or preventing neurological or neurodegenerative diseases, disorders or conditions, or for treating cancer, in particular, cancer of cells present in the CSF or central nervous system or spinal cord as well as of brain cells, in particular, astrocytes or neurons.

The present invention is based on the fact that the present inventors recognised that exosomes are secreted from the choroid plexus. The choroid plexus is a structure in the ventricles of the brain where cerebrospinal fluid is produced and which represent the blood-CSF barrier. Exosomes secreted from the plexus into the CSF contain the folate receptor alpha. Typically, the exosomes with folate receptor alpha have folate binding thereto, in particular, 5-methyltetrahydrofolate (5MTHF). Folate is an essential cofactor for methylation reactions and active transport into the central nervous system. Failure of cerebral folate transport is associated with severe neurological symptoms and results in brain atrophy and disturbed myelination.

The present invention relates in another aspect to a delivery system for the transport of components into the cerebrospinal fluid and/or brain and/or central nervous system and/or spinal cord comprising vesicles or particles and folate receptor alpha located on the outer surface of said vesicles or particles. That is, a delivery system is provided allowing targeted transport of components to predetermined sides includes the above mentioned CSF, brain and CNS or spinal cord as well as the above identified type of cells including astrocytes and neurons. The components to be transported within the delivery system are active agents as defined above including pharmaceutical active agents as well as diagnostics or other marker or label. The marker or label as used herein includes optical marker or label as well as radioactive marker or label and marker or label to be determined by other physical methods including magnetic resonance, ultrasound etc.

Preferably, the delivery system according to the present invention is a vesicular composition or vesicle comprising vesicle forming components, optionally, the component in form of an active agent associated with the vesicle forming components, and folate receptor alpha. The delivery system is particularly suitable for the delivery of pharmaceutically active agents for treating or preventing neurological or neurodegenerative diseases, disorders or conditions, or for treating cancer. For example, neurological or neurodegenerative diseases, disorders or conditions include such diseases, disorders or conditions associated with cerebral folate deficiency, e.g. cerebral folate transport deficiency, Keans-Sayre-syndrome.

In addition, examples for neurological or neurodegenerative diseases, disorders or conditions include, but are not limited to: neuronal ceroid lipofuscinoses type CLN1-CLN14 according to the nomenclature in Neurology Jul. 10, 2012 79:183-191, lysosomal storage diseases with neurological symptoms, Parkinson's Disease, Alzheimer's Disease, Huntington's Disease, dementia with Lewy bodies, multiple system atrophy, Spinocerebellar ataxia, Amyotrophic lateral sclerosis, Rett syndrome, alpha-synucleinopathies, frontotemporal lobar degenerations, prion diseases, Creutzfeldt-Jakob disease.

The cancer to be treated with the delivery system according to the present invention or the vesicle composition according to the present invention or with the pharmaceutical composition according to the present invention as defined below comprise the following types of cancer, but are not limited to: neurinomas, acoustic neuinroma, astrocytomas, lymphoma, glioma, chordoma, craniopharyngioma, medulloblastoma, metastatic brain tumors, oligodendroglioma, pituitary tumors.

The delivery system according to the present invention is particularly useful for the transport of diagnostics into the CSF and/or brain and/or central nervous system and/or spinal cord whereby the components present in the delivery system are suitable diagnostics well known to the skilled person. With the delivery system according to the present invention it is possible to transport said diagnostic to the diagnostic side in the CSF, brain, CNS or spinal cord, accordingly.

The folate receptor alpha present in the delivery system according to the present invention is preferably a human folate receptor alpha, in particular, of SEQ ID No. 1 or fragments thereof or derivate or homologs thereof.

In another aspect, the present invention relates to a method for the delivery of components, in particular, active agents, into the CSF and/or brain and/or central nervous system and/or spinal cord with the use of the delivery system or the composition according to the present invention. Said method includes the step of administering the delivery system or the vehicle composition according to the present invention into the blood or CSF of a subject. For example, administration may be effected intrathecally, intraventricually or intracranially. In addition, the administration may be effect intravenously or by manipulation of the choroid plexus.

The method as described above is useful in the diagnosis or treatment of CSF or brain or CNS or spinal cord pertaining diseases, disorders or conditions since the delivery system according to the present invention or the vehicle composition according to the present invention is able to cross the CSF-blood barrier as well as the blood brain barrier.

In a further aspect, the present invention relates to method of administering an active agent or a diagnostic to brain cells or the CNS or CSF or the spinal cord comprising providing a delivery system of vesicles or particles in folate receptor alpha located on the outer surface of said vesicles or particles and administering the same to the blood or CSF of a subject. The method according to the present invention is particularly a method for preventing or treating neurological or neurodegenerative diseases, disorders or conditions comprising administering i) a delivery system for the transport of components into the CFS and/or brain and/or central nervous system and/or spinal cord comprising vesicles or particles, optionally, an active agent associated with the vesicle forming components or the particles, and folate receptor alpha located on the outer surface of said vesicles or particles or ii) a vesicular composition or particular composition comprising vesicle forming components or particles; optionally, an active agent associated with the vesicle forming components or the particles, and folate receptor alpha to a subject in need thereof.

Finally, the present invention relates to a pharmaceutical composition or diagnostic composition containing a vehicle composition according to the present invention by a delivery system according to the present invention and pharmaceutically acceptable carrier, diluents and/or excipients. Said pharmaceutical composition or diagnostic composition is suitable for administration into the body of mammals, in particular, of humans for diagnostic or treating purposes.

BRIEF DESCRIPTION OF THE DRAWINGS

FIG. 1. FRα-mediated transport of 5MTHF in Z310 cells is stimulated by monensin and transferrin.

FIGS. 1D and 1E show apical transport of 5MTHF in primary PCPECs. Filter-grown PCPECs were loaded with 25 nM [$^3$H]5MTHF for 24 hours. Cells were then incubated with 7 µM monensin or left untreated. Radioactivity from medium samples was measured at the indicated time points. The increase of the apical [$^3$H]5MTHF concentration can be further enhanced by incubating the cells with monensin. Data are means±s.e.m. of two independent experiments, each done in triplicate.

Z310 cells stably expressing FRα were incubated with 12.5 nM [$^3$H]5MTHF alone or together with TC, MTX, PAH, probenecid and digoxin for 1 hour at 37° C. Subsequently, cells were lysed and intracellular radioactivity was measured. Only MTX at an inhibitory concentration for FRα of 10 µM significantly reduces 5MTHF uptake. Data are means±s.e.m. of three independent experiments, each done in duplicate (***, $p<0.001$; Student's t-test).

At the indicated concentrations TC inhibits transport by Oat3 and Oatp3 (Breen et al., 2004), PAH inhibits transport by Oat1, Oat3 (Sweet et al., 2002) and p-glycoprotein (Martel et al., 2006), Probenecid blocks Oat-mediated transport (Breen et al., 2004), additionally probenecid is a known inhibitor of MRP1 (Olson et al., 2002) and MRP4 (van Aubel et al., 2002). Digoxin is an inhibitor for Oatp2 (Breen et al., 2004) and MTX at a concentration of 110 nM blocks RFC-mediated uptake of 5-MTHF.

Z310 cells stably transfected with FRα, PCFT and RFC either alone or in combination as indicated, were incubated with 12.5 nM [$^3$H]5MTHF for 2 hours at 37° C. (gray bars). To block unspecific uptake, nonlabeled FA was added in an excess of 2.5 µM (black bars). Subsequently, cells were lysed and intracellular radioactivity was measured. PCFT and RFC do not contribute to FRα-mediated 5MTHF uptake in Z310 cells. Data are means±s.e.m. of three independent experiments, each done in duplicate.

Colocalization analysis of images from mouse brain sections reveal a colocalization of PKH26-stained FRα-positive exosomes and GFAP of 30%±4%. FRα negative exosomes show only a colocalization with GFAP of 4%±1.5%. Values represent means±s.e.m. (***, $p<0.001$; Student's t-test).

Plasma 5MTHF (F) is bound to FRalpha at the basolateral membrane of the choroid plexus. The 5MTHF-FRalpha complex is internalized by receptor-mediated endocytosis and translocated into GPI-anchored protein-enriched early endosomal compartments (GEEC). Multivesicular bodies (MVBs) are late endosomal compartments (LE) localized in the endocytotic route. Intralumenal vesicles of MVBs containing FRalpha are generated by inward budding of the limiting membrane. These intralumenal vesicles are released as exosomes into the CSF after fusion of the MCB with the apical membrane. Fusion of the limiting membrane of MVBs with the apical membrane explains the presence of FRalpha molecules on the apical surface of the choroid plexus cells too. FRalpha-containing exosomes circulate in the CSF, cross the ependymal cell layer and are distributed in the brain parenchyma. FRalpha-positive exosomes might initially be taken up by astrocytes and from these further delivered to neurons. FRalpha-negative exosomes hardly cross the ependymal cell layer and are targeted to other brain cells, such as microglia.

EXAMPLES

Experimental Procedures

Materials

Antibodies against the following antigens were used: human FRα (mouse monoclonal, either Mov18/ZEL; Alexis Biochemicals or NCL-L-FRalpha Clone BN3.2; Novocastra), flotillin-2 (Flot-2, mouse monoclonal; BD Biosciences), transferrin (rabbit polyclonal; Dako, Denmark), ALG-2-interacting protein X (Alix, rabbit polyclonal; Covelab), glial fibrillary acidic protein (GFAP, rabbit polyclonal; Dako, Denmark), ionised calcium binding adaptor molecule 1 (iba1, rabbit polyclonal; WAKO Chemicals, Neuss, Germany), neuron specific nuclear protein (NeuN, mouse monoclonal; Chemicon, USA), neurite outgrowth inhibitor protein A (Nogo-A, mouse monoclonal; (Oertle et al., 2003 J. Neurosci 23, 5393-5406). A rabbit polyclonal antibody against human PCFT was kindly provided by 1. David Goldman (Bronx, N.Y., USA). Secondary antibodies were purchased from Dianova (Hamburg, Germany). Folic acid conjugated to fluorescein isothiocyanate (FA-FITC) was kindly provided by Philip S. Low (West Lafayette, Ind., USA). Phosphatidylinositol-specific phospholipase C from *Bacillus cereus* (PI-PLC) was from Sigma.

The following inhibitors were used: taurocholate (TC), methotrexate (MIX), p-aminohippuric acid (PAH), probenecid, digoxin, brefeldin A (BFA) and N-ethylmaleimide (NEM). All were purchased from Sigma.

Cell Cultures and Transfections

Cloning of FRα cDNA has been described previously (Steinfeld et al., 2009: Am J Hum Genet 85, 354-363). For expression in immortalized rat choroid plexus epithelial cells Z310 FRα or PCFT cDNA was subcloned into the NheI/HindIII sites of pcDNA3.1 Hygro(+) (Invitrogen). For double mutant FRα/PCFT Z310, PCFT cDNA was subcloned into the NheI/HindIII sites of pcDNA3.1 Zeo(+) (Invitrogen). RFC cDNA was subcloned into the NheI/EcoRI sites of pEFIRES-P.

Z310 cells were grown in DMEM supplemented with 10% fetal calf serum, 2 mM glutamine, 100 U/mL penicillin, 100 µg/mL streptomycin, 200 µg/mL G418 (Roth, Karlsruhe, Germany) and 10 ng/mL epidermal growth factor (Invitrogen).

Transfections were done using Effectene transfection reagent (Qiagen) and stable Z310 cell clones were selected in the presence of 400 µg/mL hygromycin B (PAA Laboratories, Pasching, Austria), 250 µg/mL Zeocin, or 1 µg/mL Puromycin (Invitrogen), respectively. Stable transfectants of MDCK or HepG2 cells were selected in the presence of 800 µg/mL G418.

Porcine choroid plexus epithelial cells (PCPECs) were prepared basically as described previously (Hakvoort et al., 1998: J Neurochem 71, 1141-1150). Isolated PCPECs were seeded in laminin-coated transwell culture plates (0.4 µm pore size, Costar, Cambridge, Mass.) with a diameter of 12 mm using a seeding density of 20 mg wet tissue/cm2. The cell culture medium (DMEM-Ham's F-12, Biochrom, Berlin, Germany) was supplemented with 10% fetal calf serum, 4 mM glutamine, 5 µg/ml insulin, 100 U/mL penicillin and 100 µg/mL streptomycin. Cytosine arabinoside (20 µM) was added to suppress the growth of contaminating cells. After reaching confluence at days in vitro (DIV) 8, growth medium was replaced by serum-free culture medium (SFM) to support cell differentiation and improve barrier function. At DIV 10, the medium was replaced by folate-free RPMI medium (Invitrogen) without serum. The transport experiments were performed on cells at DIV 13-15 that exhibited high transepithelial electrical resistance (TEER) of about 1000Ω×cm2.

Disassociated neonatal cortices from postnatal day 0-2 mice were cultured in DMEM supplemented with 10% fetal calf serum, 1% GlutaMAX (Invitrogen), 100 U/mL penicillin and 100 µg/mL streptomycin on laminin- and poly-L-lysin-coated coverslips at 37° C. in 5% CO2. Medium was changed every 3-4 days. At DIV 7-14, mixed cortical cultures consisting of oligodendrocytes, cortical neurons and microglia on an astrocyte monolayer were obtained.

Transcytosis Assays

Transcytosis assays were adapted from Polishchuk et al, 2004 (Polishchuk et al., 2004: Nat Cell Biol 6, 297-307). Before the experiments, cells were maintained in folate-free RPMI 1640 medium. Filter-grown Z310 cells stably expressing FRα were washed with HBS [20 mM HEPES, 140 mM NaCl, 5 mM KCl, 2 mM MgCl2, 5 mM glucose (pH 7.4)] and incubated on ice for 15 min with 100 nM FITC-labeled folic acid (FA-FITC) together with anti-human FRα antibody (Mov18/ZEL) added to the basolateral chamber of the transwell plate. Filters were washed three times with HBS (ice-cold) and some filters were fixed immediately after incubation on ice. The others were shifted to 37° C. for the indicated time points, fixed and prepared for confocal microscopy. Biochemical evaluation of transcytosis was based on the idea that removal of protein from the basolateral surface will result in decrease of its amount at the apical domain of the plasma membrane. Therefore, filter-grown Z310 cells stable expressing FRα were incubated with PI-PLC added to the basolateral medium for the indicated time points to remove FRα from the basolateral surface of the cells. To detect the apical portion of FRα, cells were washed and PI-PLC was added to the apical medium 30 min on ice to harvest the receptor from the apical domain of the plasma membrane. Samples were than subjected to SDS-PAGE and western blotting with an anti-human FRα antibody (NCL-L-FRalpha).

Exosome Preparation

Exosomes were prepared from human CSF or from cell culture supernatant by performing sequential centrifugation. Therefore CSF or supernatant from Z310 cells was centrifuged for 15 min at 1500×g to remove debris. The supernatant was then subjected to ultracentrifugation at 10.000×g for 45 min and at 100.000×g for 150 min. The collected pellets were finally resuspended in CellLytic™ M Cell Lysis Reagent (Sigma) and subjected to SDS-PAGE and western blot analysis. For sucrose gradient analysis, a discontinuous sucrose density gradient was prepared by sequential layering of 2.0, 1.75, 1.5, 1.25, 1.0, 0.75, 0.5 and 0.25 M sucrose (w/w) in 20 mM HEPES, 2 mL each. The exosome samples were layered on top of the gradient and centrifuged for 16 hours at 100.000×g. Subsequently, fractions were collected, diluted 1:4 in PBS and centrifuged at 100.000×g for 70 min. Pellets were resuspended in Laemmli sample buffer and subjected to western blot analysis.

For immunofluorescence analysis, the exosome pellet was resuspended in PBS and stained with PKH26 (Sigma). The staining reaction was stopped after 5 min with exosome-free FCS. Exosomes were then washed in PBS and pelleted by ultracentrifugation (100.000×g, 70 min).

For electron microscopy analysis, exosomes were prepared and the pellet was washed once in a large volume of PBS. Exosomes were then fixed with 4% paraformaldehyde and absorbed to glow discharged formvar-carbon coated copper grids. The samples were immunolabeled with anti-human FRα antibody (Mov18/ZEL) or anti-human Flotillin-2 antibody followed by a rabbit anti-mouse antibody. The antibodies were detected with Protein A coupled to 10 nm gold particles. After contrasting by neutral uranyl acetate and picking up with a wire loop from methylcellulose-uranyl acetate, samples were imaged on a Leo EM912AB-electron microscope (Zeiss) and images were acquired using on axis 2048×2048 charge-coupled device camera (Proscan, Schering).

Western Blot Analysis

Immunoblot analysis was conducted using standard techniques. Briefly, the samples were denatured for 10 min at 95° C. in Laemmli sample buffer, subjected to SDS-PAGE (12% gel) and transferred to nitrocellulose membranes. The membranes were probed with a mouse monoclonal anti-human FRα antibody (NCL-L-FRalpha) and a rabbit polyclonal anti-human transferrin antibody. As antibodies against exosomal markers rabbit polyclonal antibody to Alix and mouse monoclonal Flot-2 were used. First antibodies were detected by using the appropriate secondary antibodies conjugated to horseradish peroxidise (HRP). The bands were visualized by chemiluminescence using Lumi Light Western blotting substrate (Roche Diagnostics, Mannheim, Germany).

Immunofluorescence Microscopy and Image Analysis

Confocal images were acquired on a spinning disk confocal imaging system (UltraView®, Perkin-Elmer). The system incorporated an Olympus IX81 inverted microscope using a 100×1.4 NA lens. Excitation wavelengths and filter sets for FITC and Cy3 were as supplied by the manufacturer. Fixed cells labeled with antibodies and/or FA-FITC were optically sectioned into z-stacks. Image processing was performed using the Zeiss LSM image browser software and NIH ImageJ (http://rsbweb.nih.gov/ij; Open Source). Colocalization analysis for the internalization assay was done by using the "Co localization Threshold" algorithm from ImageJ. Images from at least 20 slides per mouse brain were analyzed and data presented in the figure were from two independent experiments. Normal distribution of the data was analyzed with D'Agostino-Person normality test and significance was tested using Student's t-test.

High-Resolution Stimulated Emission Depletion (STED) Microscopy

Exosomes were prepared and the pellet was washed once in a large volume of PBS. The exosomes were directly fixed on glass coverslips with 4% paraformaldehyde. Two-color STED microscopy was performed, using sheep anti-mouse polyclonal antibody labeled with Atto590 (for anti-human FRα as first antibody) and goat anti-rabbit polyclonal antibody conjugated to Atto647N (for Alix as marker for exosomes). The colocalization of FRα and Alix was analyzed by using the "Colocalization Threshold" algorithm from ImageJ.

FRα-Mediated 5MTHF Uptake and Transport Analysis

For 5MTHF uptake and transport measurements in Z310 cells, 4.2*104 cells were seeded in laminin coated transwell culture plates (0.3 cm2 growth area, 0.4 µm pore size) in folate-free RPMI medium. To test the barrier function, dye permeability assays with lucifer yellow were performed. Cells were used for experiments when the permeability was below 1% per hour. 72 hours postconfluent, cells were loaded with 12.5 nM [$^3$H]5MTHF in pre-warmed folate-free RPMI medium containing 1% BSA added either to the apical (350 µL) or basolateral (700 µL) chamber of the transwell plates. [3',5',7,9-$^3$H](6S)-5MTHF was purchased from Moravek Biochemicals (Brea, Calif.). Cells were then incubated at 37° C. for 1 hour and were subsequently washed three times with folate-free RPMI medium. Fresh RPMI medium was added containing either 7 µM monensin (Sigma) or 0.5 mg/mL rat transferrin (Rockland, Gilbertsville, Pa.) and cells were then incubated at 37° C. in 5% CO2. Samples were removed from the apical and basolateral medium at the indicated time points. To stop the transport experiment, the transwell plates were placed on ice and the cells were washed three times with ice-cold HBS. Cells were than dissolved in 0.2 M NaOH and protein determination was done with the BCA protein assay (Pierce, Rockford, Ill.). Radioactivity in medium samples and cell lysates was measured in a liquid scintillation spectrometer.

Immunohistochemistry of Choroid Plexus

Paraffin sections of human choroid plexus from postmortem autopsy blocks were retrieved from the department of Neuropathology, University of Göttingen, Germany. Immunohistochemistry was carried out as previously described (Letiembre et al., 2009). In brief, after deparaffinization, slides were pre-treated by heating in a microwave in citrate buffer (10 mM, pH 6.0) followed by incubation in guanidinthiocyanate (4 M) for 25 min. For staining with HRP-conjugated secondary antibody, endogenous peroxidase was blocked by incubation in 3% H2O2 for 20 min. Staining on human sections was performed using mouse monoclonal FRα antibody (NCL-L-FRalpha) or rabbit polyclonal PCFT antibody followed by HRP-conjugated anti-mouse antibody. After development, the slides were counterstained with hematoxylin. For immunofluorescence, the sections were treated as described above except the use of secondary Alexa 488 donkey anti-mouse or Alexa 546 donkey anti rabbit antibodies.

Internalization Assay

Mixed cortical cultures were obtained form neonatal mice and immediately plated on coverslips and incubated in the respective growth medium. Before the internalization assay, exosomes were purified from Z310 cells, stably transfected with FRα or vector and labelled with PKH26 and FA-FITC as described above. The uptake was performed by incubating the cell cultures with exosome dilutions for 2 hours at 37° C. and 5% CO2. Cells were then fixed, permeabilized and stained with the respective antibodies for immunofluorescence analysis.

In vivo experiments were carried out with C57BL/6 mice at the ages between 80 days and 100 days. The mice were anesthetized with ketamine (100-125 mg/kg) and xylazine (10-12.5 mg/mL) and the intraventricular cannulas were stereotaxically implanted into the lateral ventricle as described previously (Hung et al., 1984: Eur J Pharmacol 106, 645-648). 10 µL of labelled exosome solution were injected into the intraventricular cannula 4 hours before the mice were euthanized. Intact brains were then dissected, immediately frozen in liquid nitrogen pre-cooled isopentane and stored at −20° C. For fluorescence analysis, the frozen brain tissues were cryosectioned to a thickness of 10 µm. The frozen sections were fixed in methanol for 5 min at −20° C. After washing in PBS, sections were blocked for 1 hour in PBS containing 10% donkey serum (Sigma), followed by overnight incubation with primary antibodies in block buffer at 4° C. Sections were than washed in PBS, incubated with secondary Alexa 488 donkey anti-rabbit antibody and mounted using Slowfade Gold anti-fade reagent (Invitrogen).

Results

Transcellular Transport of 5MTHF Across the Choroid Plexus is Mediated by FRα

To elucidate the transcellular transport of 5MTHF across the choroid plexus we investigated the directed movements of radioactively labelled 5MTHF in Z310 cells as well as in primary porcine choroid plexus cells.

Figure 1A:
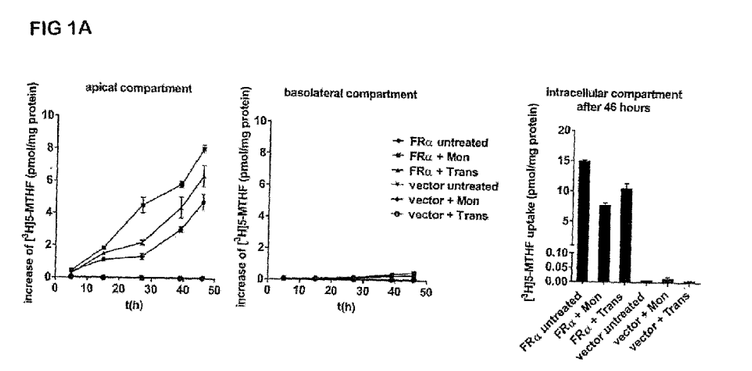
FIG. 1A shows a filter-grown Z310 cells stably transfected with FRα or vector were loaded with [$^3$H]5MTHF for 1 hour. After three washing steps, cells were incubated with fresh RPMI medium containing either 7 µM monensin (Mon) or 0.5 mg/ml rat transferrin (Trans) or contained no supplementation. Samples from the apical and basolateral compartment were removed at the indicated time points. Subsequently, cells were lysed and radioactivity was measured in medium samples and cell lysates. Data are means±s.e.m. of three independent experiments.
Figure 1B:
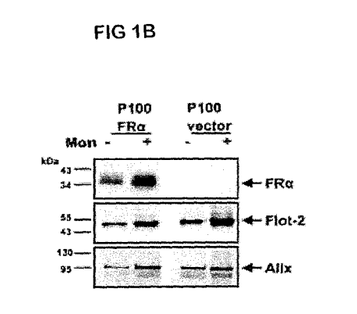
FIG. 1B shows Z310 cells stably transfected with FRα or vector were treated with 7 monensin for 22 hours. The medium was collected and subjected to ultracentrifugation for exosome purification. The P100 pellets were subjected to western blots and probed with antibodies against FRα, Flot-2 and Alix.
Figure 1C:
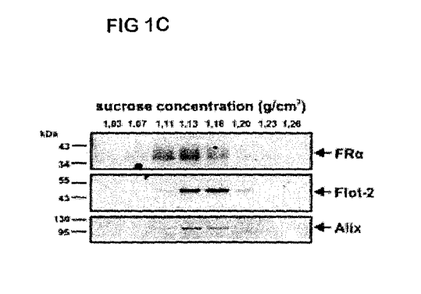
FIG. 1C—further characterizes the vesicles derived from Z310 cells, the 100.000×g pellet from monensin treated Z310 cells stably expressing FRα was subjected to sucrose gradient ultracentrifugation. FRα is mainly enriched in the same fractions that contained Flot-2 and Alix.

FRα-transfected or vector-transfected Z310 cells were grown in a two chamber transwell system and [$^3$H]5MTHF was either given into the basolateral or apical compartment. After a 1 h incubation with [$^3$H]5MTHF the medium was replaced by fresh medium and the time-dependent emergence of [$^3$H]5MTHF in both compartments was detected. Notably, 5MTHF was only released into the apical compartment of FRα-transfected cells but not of vector-transfected cells and the apical shedding of [$^3$H]5MTHF was increased by the addition of either monensin (70% increase) or transferrin (36% increase) (FIG. 1A). The monensin- or transferrin-dependent increase in apical release occurred at the expense of the intracellular [$^3$H]5MTHF uptake. Whether Z310 cells were loaded with [$^3$H]MTHF from the apical or basolateral site did not significantly alter the rate of apical shedding. But no significant basolateral release of [$^3$H] 5MTHF could be detected under any condition. These data suggest a exosomal type of FRα-mediated transport of 5MTHF into the apical compartment since it is known that monensin and transferrin induce exosome release from cells. The vesicular nature of the directed FRα-dependent transport was confirmed by fractionation of the cell culture supernatant. FR was enriched in the P100 (100.000×g pellet) fraction and was co-purified with the exosomal markers Flot-2 and Alix (FIG. 1B). The monensin-induced increase in FRα signal was proportional to the increase in Flot-2 and Alix release. Flot-2 and Alix release was also induced by monensin in vector-transfected cells in the absence of FRα. The vesicle-containing P100 fraction of FRα-transfected and monensin treated Z310 cells was subjected to sucrose gradient ultracentrifugation. Very similar to human CSF, FRα was mainly recovered from fractions possessing the characteristic density of exosomes (between 1.11 and 1.16 g/cm3) and containing the exosomal markers Flot-2 and Alix (FIG. 1C).

In addition, the vesicles showed the typical size of exosomes and showed colocalization of FRα and Alix in two-color STED microscopy. Quantitative analysis revealed a colocalization of 63%±8% of FRα and Alix. These data demonstrate that exosomes derived from the supernatant of FRα-transfected Z310 cells share major characteristics with exosomes derived from human CSF. The fact that quantitative analysis of STED images achieved a higher percentage of FRα colocalization with the exosomal marker Alix can be explained by the FRα overexpression in 2310 cells.

We also compared the protein composition of exosome preparations derived from Z310 cells with the one purified from human CSF by mass spectrometry (Table 1). Both preparations contained 22 of 25 commonly accepted exosomal markers (http://exocarta.org/exosome_markers) and showed an overall similar protein profile.

TABLE 1

Mass spectrometry analysis of exosomes purified from human CSF and Z310 cells

| human CSF | Z310 vector-transfected | Z310 FRα-transfected |
| --- | --- | --- |
| glyceraldehyde-3-phosphate dehydrogenase (GAPDH) | glyceraldehyde-3-phosphate dehydrogenase (GAPDH) | glyceraldehyde-3-phosphate dehydrogenase (GAPDH) |
| ALG-2 interacting protein X (Alix) | ALG-2 interacting protein X (Alix) | ALG-2 interacting protein X (Alix) |
| flotillin-1 | flotillin-1 | flotillin-1 |
| flotillin-2 | flotillin-2 | flotillin-2 |
| folate receptor α | — | folate receptor α (human) |
| tumor suspectibility gene 101 (TSG101) | tumor suspectibility gene 101 (TSG101) | tumor suspectibility gene 101 (TSG101) |
| CD63 | CD63 | CD63 |
| transferrin receptor protein (CD71) | transferrin receptor protein (CD71) | transferrin receptor protein (CD71) |

Exosome preparations from human CSF and Z310 cells were analyzed by mass spectrometry. Each preparation contained a couple of hundred proteins with a high probability of over 95%. Among these we could identify FRα in the sample derived from human CSF as well as in FRα-transfected 2310 cells. Although expression of endogenous rat FRα in Z310 cells has previously been indicated by RT-PCR (Halwachs et al. 2011) the rat FRα expression might be under the mass spectrometric detection level. Exosomal markers like ALG-2 interacting protein X (Alix), flotillin-1 (Flot-1), flotillin-2 (Flot-2), CD63, tumor susceptibility gene 101 (TSG101) and transferrin receptor (CD71) could consistently be detected in all exosome preparations indicating a similar composition of exosomes derived from Z310 cells when compared with exosomes purified from human CSF. The order in Table 1 represents semiquantitative incidence of proteins determined by the ranking of unweighted spectrum counts in the program Scaffold 3. Compared with the 25 most frequently identified proteins in exosomes (http://exocarta.org/exosome_markers) we found 22 (88%) (human CSF) and 21 (84%) (Z310 cells) identity, respectively.

Figure 1D:
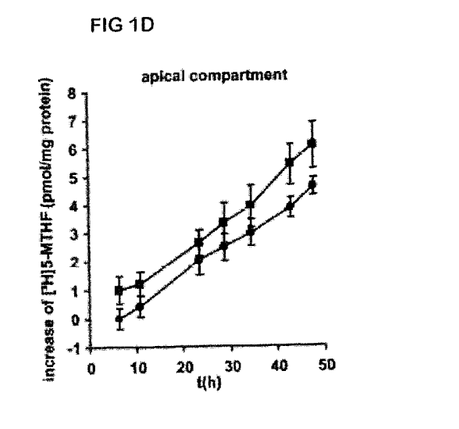
Figure 1E:
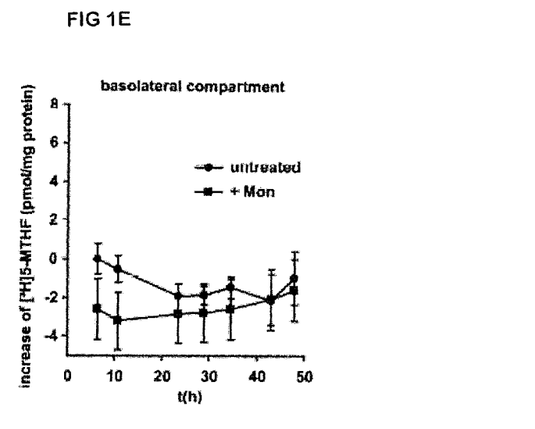

To validate our findings in Z310 cells, we studied the directional 5MTHF transport in primary porcine choroid plexus epithelial cells (PCPEC). Filter-grown PCPEC were loaded with 25 nM [$^3$H]5MTHF for 24 hours. Subsequently, medium was changed and cells were treated with 7 µM monensin or left untreated. A significant increase of radioactivity could only be observed in the apical compartment (FIG. 1D). Treatment of cells with monensin further enhanced the apical accumulation of [$^3$H]5MTHF by 33%. The rate of transport into the apical compartment corresponds to the one obtained for FRα-transfected Z310 cells. And equivalent to Z310 cells, no significant [$^3$H]5MTHF release into the basolateral compartment could be detected.

Figure 2:
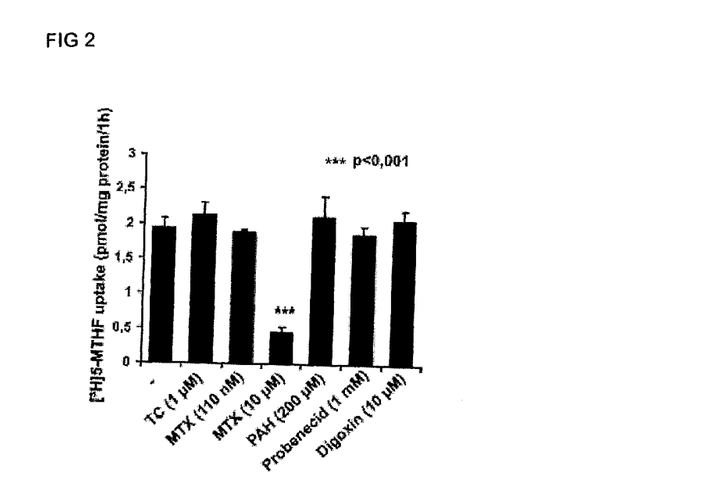
FIG. 2. Uptake of 5MTHF is not reduced by inhibition of organic anion transporters in Z310 cells stably expressing FRα.

We performed additional experiments to evaluate FRα-independent transport processes in Z310 cells at physiological MTHF concentration (12.5 nM). A couple of organic anion transporters are known to be expressed in Z310 cells (Halwachs et al., 2011). Contribution of Oat1, Oat3, Oatp2, Oatp3, Mrp1, Mrp4, p-glycoprotein (Mdr1) and RFC to 5MTHF uptake into FRα-transfected Z310 cells was assessed by the incubation of cells with the following inhibitors of these transporters: taurocholate (TC), methotrexate (MTX), p-aminohippuric acid (PAH), probenecid and digoxin. As illustrated in FIG. 2, none of the inhibitors reduced the uptake of [$^3$H]5MTHF with the exception of MTX that significantly reduced 5MTHF uptake at a concentration of 10 µM. At this concentration MTX is known to block FR-mediated MTHF binding as well.

Figure 3:
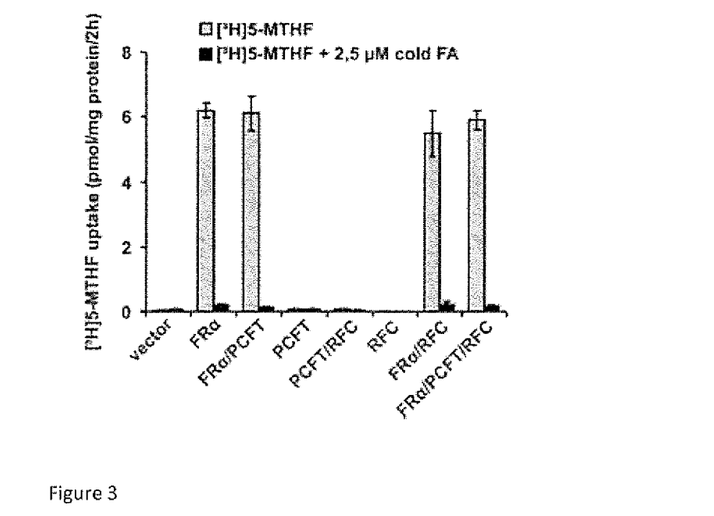
FIG. 3. Contribution of PCFT and RFC on FRα-mediated 5MTHF uptake in Z310 cells.

The contribution of the PCFT and the RFC to FRα-mediated 5MTHF uptake into Z310 cells was studied by stable cotransfection of FR with PCFT or RFC or a combination of both (FIG. 3). Transfection of FRα increased the 5MTHF uptake 248-fold when compared to the vector-transfected control cells. Transfection of PCFT or RFC or the combination of both did not significantly alter 5MTHF uptake into Z310 cells when compared with the control cells. In case of the double transfectants FRα/PCFT and FRα/RFC or for the triple transfectant FRα/PCFT/RFC no further increase of 5MTHF uptake was observed when compared to the FRα-transfected cells (FIG. 3). These data indicate that at least at the physiological 5MTHF concentrations in plasma (4-20 nM) the uptake of 5MTHF into the choroid plexus is primarily mediated by FRα.

FRα Positive Exosomes are Selectively Internalized by Astrocytes

Figure 4:
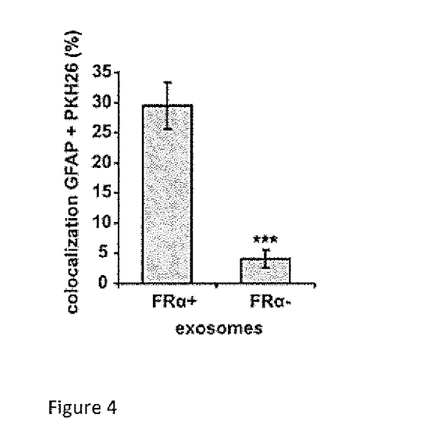
FIG. 4. FRα containing exosomes are selectively internalized by astrocytes in vivo and in vitro.

We have unexpectedly disclosed FRα as exosomal cargo in the CSF. To further understand the biological function of this transport mechanism we injected exosomes derived from FRα-transfected or vector-transfected Z310 cells into the lateral ventricle of C57BL/6 mice. Purified exosomes were labelled with the dye PKH26 before they were applied via stereotactically implanted intraventricular cannulas. 4 h post injection the mice were euthanized and their brains immediately frozen. Immunohistochemistry of the mouse brain sections revealed that FRα-positive exosomes penetrated into the brain parenchyma and colocalized with GFAP-positive astrocytes. In contrast, FRα-negative exosomes were mainly detected in the periventricular ependyma and did not colocalize with GFAP positive cells. Quantitative analysis revealed a 30% colocalization of PKH26-labelled FRα-positive exosomes with GFAP-positive cells but less than 4% colocalization in case of FRα-negative exosomes (FIG. 4). To validate our in vivo findings we incubated primary mixed cortical cultures obtained from neonatal mice with either PKH26-labelled exosomes, with FA-FITC or a combination of both. After incubating the cells for 2 hours at 37° C., cells were fixed and analyzed by immunofluorescence microscopy. FRα-positive exosomes were selectively taken up by GFAP-positive astrocytes and no significant colocalization was obtained with cells stained with markers for microglia, neurons and oligodendrocytes. FRα-negative exosomes did not colocalized with astrocytes but were internalized by Iba1-positive microglia. FA-FITC was also delivered to astrocytes when combined with FRα-positive exosomes. However, none of the cell types internalized free FA-FITC.

Discussion

Figure 5:
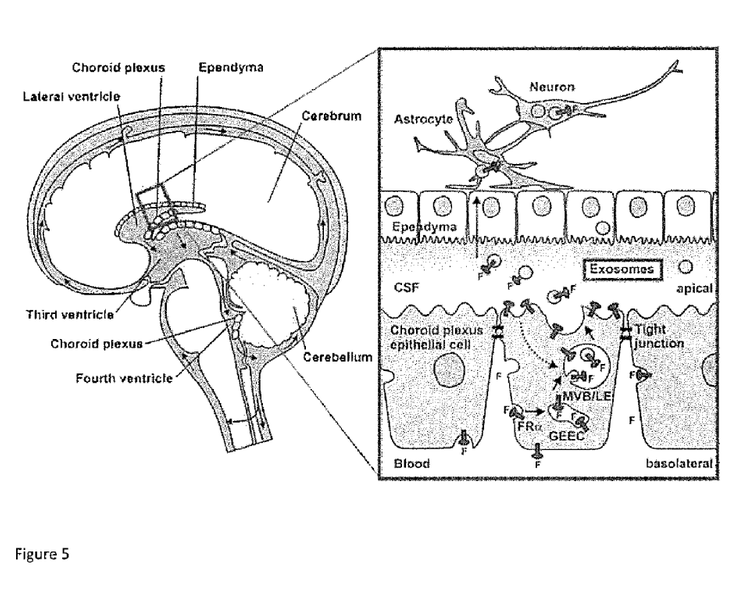
FIG. 5. Suggested model of cerebral folate transport

Several characteristics of FRα argue for its pivotal role for the 5MTHF transport across the blood-CSF barrier. Within the brain FRα is almost selectively expressed in the choroid plexus and its high binding affinity for folates (Kb 1-10 nM) perfectly matches the physiological 5MTHF concentration in human plasma (4-20 nM). Further, a hereditary FRα defect is associated with extremely low 5MTHF concentrations in the CSF (equal or below 5 nM) and causes a childhood onset neurodegenerative disease (Steinfeld et al., 2009: Am J Hum Genet 85, 354-363; Grapp et al., 2012: Brain 135, 2022-2031). Our experiments with polarized cells (Z310 cells) demonstrate a basolateral to apical sorting of FRα that provides for receptor-mediated endocytosis and transcytosis of folates. It is known that internalized GPI-anchored proteins such as FRα enter the endosomal compartment by a clathrin-independent pathway to form tubular early endocytic compartments called GPI-anchored protein enriched endosomal compartments (GEECs). During the subsequent endosomal maturation process multivesicular bodies are formed that contain intralumenal vesicles. Multivesicular bodies are known to be sites for intracellular sorting of proteins between recycling, degradation and secretion pathways. We have provided several lines of evidence that in choroid plexus cells FRα-containing multivesicular bodies fuse with the apical membrane and secrete their intralumenal vesicles as exosomes (FIG. 5). We further suggest that FRα recycles between the apical membrane and the late endosomal compartment and thus offer 5MTHF uptake from the CSF as well. And we speculate that the third key folate transporter the PCFT may be responsible for the cytoplasmic 5MTHF transport out of acidified endosomal compartments. The lacking alterations in folate transport after transfection of the PCFT and the RFC or after addition of various inhibitors of OATs support the unique role of FRα during the transcellular 5MTHF transport in Z310 choroid plexus cells. These results are consistent with other studies on primary rat choroids plexus epithelial cells that showed two separate folate uptake mechanisms (Wollack et. Al., J. Neurochem, 2008, 104(6), 1494-1503). One FRα-dependent process mediates efficient uptake of 5MTHF at low extracellular folate concentrations (Km ~9.5 nM). The other way of internalization is independent of the FRα but likely depends on OAT such as the RFC and accounts for folate uptake at higher concentrations (Km ~766 nM). It is likely that any unbound 5MTHF released into the CSF will be picked up by membrane-bound FRα to recycle within the choroid plexus cells and will ultimately be secreted into CSF while bound to exosome-attached FRα. This unusual transport mechanism might serve as a stabilizing and buffering system for fluctuations in folate supply and demand of the brain. Most excitingly, our results indicate that the FRα-exosome transport vehicle is crucial for 5MTHF targeting to astrocytes. Interestingly, exosomes from both human CSF as well as Z310 cells contained several enzymes of folate metabolism, notable C-1-tetrahydrofolate synthase, 10-formyltetrahydrofolate dehydrogenase, and dihydrofolate reductase (Table 1). This implies that 5MTHF carrying exosome additionally provide enzymes essential for folate metabolism to their target cells.

Our studies disclosed the mechanism of cerebral folate transport deficiency and extended this entity to other disorders, such as Kearns-Sayre syndrome that affect the choroid plexus. The functional loss of PCFT may also compromise the choroid plexus function providing an explanation why patients with hereditary malabsorption show low 5MTHF concentration in the CSF even if they are supplemented with oral folate.

The unexpected role of exosomes as transport medium for micronutritions and the impact of FRα expression on exosomal targeting stimulate further therapeutic applications for exosomes.

The invention claimed is:

1. A vesicle composition comprising
a vesicle forming component selected from at least one of a lipid, exosome, liposome, nanostructured vesicle, micelle, erythrocyte ghost, organic particle, inorganic particle, colloidal particle, nanoparticle, and composite particle, and
human folate receptor alpha located on the outer surface of said vesicle forming component or a folate receptor alpha from a mammal selected from the group consisting of mouse, horse, cow, pig, dog, and cat located on the outer surface of said vesicle forming component.

2. The vesicle composition according to claim 1 wherein the vesicle forming component is a lipid.

3. The vesicle composition according to claim 1 wherein the human folate receptor alpha is SEQ ID No. 1.

4. A pharmaceutical composition containing a composition according to claim 1 and a pharmaceutically acceptable carrier, diluent or excipient.

5. The vesicle composition according to claim 1 wherein the lipid is a vesicle forming membrane.

* * * * *

SEQUENCE LISTING

```
<160> NUMBER OF SEQ ID NOS: 2

<210> SEQ ID NO 1
<211> LENGTH: 257
<212> TYPE: PRT
<213> ORGANISM: homo sapiens

<400> SEQUENCE: 1

Met Ala Gln Arg Met Thr Thr Gln Leu Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60
```

```
Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
                 85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser
```

<210> SEQ ID NO 2
<211> LENGTH: 1147
<212> TYPE: DNA
<213> ORGANISM: homo sapiens

<400> SEQUENCE: 2

```
tggaggcctg gctggtgctc acatacaata attaactgct gagtggcctt cgcccaatcc      60
caggctccac tcctgggctc cattcccact ccctgcctgt ctcctaggcc actaaaccac     120
agctgtcccc tggaataagg caaggggagn tgtagagcag agcagaagcc tgagccagac     180
ggagagccac ctcctctccc agggacagac atggctcagc ggatgacaac acagctgctg     240
ctccttctag tgtgggtggc tgtagtaggg gaggctcaga caaggattgc atgggccagg     300
actgagcttc tcaatgtctg catgaacgcc aagcaccaca aggaaaagcc aggccccgag     360
gacaagttgc atgagcagtg tcgaccctgg aggaagaatg cctgctgttc taccaacacc     420
agccaggaag cccataagga tgtttcctac ctatatagat caactggaa ccactgtgga     480
gagatggcac ctgcctgcaa acggcatttc atccaggaca cctgcctcta cgagtgctcc     540
cccaacttgg ggccctggat ccagcaggtg gatcagagct ggcgcaaaga gcgggtactg     600
aacgtgcccc tgtgcaaaga ggactgtgag caatggtggg aagattgtcg cacctcctac     660
acctgcaaga gcaactggca caagggctgg aactggactt caggtttaa caagtgcgca     720
gtgggagctg cctgccaacc tttccatttc tacttcccca cacccactgt tctgtgcaat     780
gaaatctgga ctcactccta caaggtcagc aactacagcc agggagtgg ccgctgcatc     840
cagatgtggt tcgacccagc ccagggcaac cccaatgagg aggtggcgag gttctatgct     900
gcagccatga gtggggctgg gccctgggca gcctggcctt tcctgcttag cctgccccta     960
atgctgctgt ggctgctcag ctgacctcct tttaccttct gatacctgga aatcccctgcc   1020
```

| | |
|---|---|
| ctgttcagcc ccacagctcc caactatttg gttcctgctc catggtcggg cctctgacag | 1080 |
| ccactttgaa taaaccagac accgcacatg tgtcttgaga attatttgga aaaaaaaaaa | 1140 |
| aaaaaaa | 1147 |